(12) United States Patent
Mustacich et al.

(10) Patent No.: US 6,530,260 B1
(45) Date of Patent: Mar. 11, 2003

(54) GAS CHROMATOGRAPHY ANALYSIS SYSTEM

(75) Inventors: Robert V. Mustacich, Santa Barbara, CA (US); John P. Richards, Santa Barbara, CA (US); James F. Everson, Santa Barbara, CA (US)

(73) Assignee: RVM Scientific, Inc., Santa Barbara, CA (US)

( * ) Notice: Subject to any disclaimer, the term of this patent is extended or adjusted under 35 U.S.C. 154(b) by 0 days.

(21) Appl. No.: 10/061,230

(22) Filed: Feb. 4, 2002

(51) Int. Cl.[7] ............ G01N 1/00; G01N 25/00; G01N 30/02; B01D 15/08
(52) U.S. Cl. ............ 73/23.41; 73/23.25; 210/198.2; 422/89
(58) Field of Search .............. 73/23.41, 23.42, 73/23.25, 23.39; 210/198.2; 422/89; 95/17, 102, 105

(56) References Cited

U.S. PATENT DOCUMENTS

| | | |
|---|---|---|
| 3,159,996 A | 12/1964 | Norem |
| 4,269,710 A | 5/1981 | Hunt |
| 4,305,276 A | 12/1981 | Mueller |
| 4,420,679 A | 12/1983 | Howe |
| 4,752,216 A | 6/1988 | Hurrell |
| 4,869,876 A | 9/1989 | Arfman et al. |
| 5,005,399 A | 4/1991 | Holtzclaw et al. |
| 5,014,541 A | 5/1991 | Sides et al. |
| 5,340,543 A | 8/1994 | Annino et al. |
| 5,467,635 A | 11/1995 | Nakagawa et al. |
| 5,634,961 A | 6/1997 | Gordon |
| 5,665,314 A | 9/1997 | Berger et al. |
| 5,686,655 A | 11/1997 | Itoi |
| 5,782,964 A | 7/1998 | Mustacich |
| 5,830,262 A | 11/1998 | Marchini et al. |
| 5,830,353 A | 11/1998 | Henderson |
| 5,979,221 A | 11/1999 | Walte et al. |
| 6,004,514 A | 12/1999 | Hikosaka et al. |
| 6,093,921 A | 7/2000 | Gaisford et al. |
| 6,209,386 B1 | 4/2001 | Mustacich et al. |
| 6,217,829 B1 | 4/2001 | Mustacich et al. |
| 6,223,584 B1 | 5/2001 | Mustacich et al. |

Primary Examiner—Hezron Williams
Assistant Examiner—J L Politzer
(74) Attorney, Agent, or Firm—Rosenberg, Klein & Lee

(57) ABSTRACT

A gas chromatography system includes a gas chromatography oven having a door adapted for integration with gas chromatography modules which are located outside of the oven cavity. For these purposes, the oven door has module receiving openings in which the modules are secured. The gas chromatography module includes a module housing containing a main coil of the capillary column, a pair of transfer lines sleeved on the free ends of the capillary column, a heater wire wound on the transfer lines, and, optionally, a pair of chromatography connectors which extend into the oven cavity and through which the free ends of the capillary column, as well as transfer lines, projecting into the oven cavity. A wall of the GC oven has an injector port and a detector port for injection of a sample into the oven cavity and for detecting the sample constituents. Column lengths extend within the oven cavity between the module and injector and detector, respectively. An electronic control block is positioned outside the oven cavity and mounted on the door in proximity to the modules to control the heating of the transfer line of the module.

16 Claims, 10 Drawing Sheets

GAS CHROMATOGRAPHY ANALYSIS SYSTEM

FIELD OF THE INVENTION

The present invention relates to gas chromatography systems for generally continuously sampling chemical samples and detecting desired compounds therefrom. In particular, the subject invention is directed to gas chromatographic (GC) column modules for temperature programmed analysis as well as a gas chromatography oven having a door (or a wall) designed specifically to be removably integrated with the column GC modules external the oven cavity in order that the GC oven may be operated isothermically at an elevated temperature for efficient gas chromatography analysis.

Moreover, the present invention relates to a gas chromatography system which includes capillary gas chromatographic column members, temperature sensing mechanisms and heating mechanisms formed into gas chromatographic column modules which are located at the door of a gas chromatography oven in a manner to optimize thermal effect and produce an overall low power consumption system.

BACKGROUND OF THE INVENTION

In the field of gas chromatography, sample tests are typically administered in a temperature controlled oven. For example, as described in U.S. Pat. Nos. 4,420,679; 5,665,314; and, 5,830,353, a capillary GC column which is usually contoured as an extended tube wound in a generally circular fashion is suspended in the GC oven between a sample injector and a sample detector.

The temperature programming of capillary gas chromatography columns is standardly practiced by electronic control of the temperature of a GC oven containing the gas chromatography column. To achieve rapid and uniform temperature response of the gas chromatography column assembly to temperature changes in the oven, capillary gas chromatography columns are standardly packaged by winding the columns on a wire frame support. The winding of the columns on the wire frame support provide extensive surface contact of the capillary gas chromatography column with the heated air in the oven for rapid temperature calibration of the capillary gas chromatography column with the oven air. In laboratory gas chromatography ovens, the air within the oven is typically mixed with a fan to achieve temperature uniformity within the oven.

When a sample is injected through the injector port, it travels through the column until it reaches the detector port. For the standard practice of temperature programming in gas chromatographic analysis, the temperature in the oven containing the gas chromatography column is gradually increased to extend the range of gas chromatography separation capability. The use of capillary columns have become standard practice in laboratory gas chromatography instrumentation and the wide range of separation capability has been made possible through variation of the chemical compositions of the polymers which coat the inner walls of the capillary gas chromatography column. A number of polymer coatings are commercially available for capillary gas chromatography columns having standard thickness, column length, and column inner diameters to optimize the chemical separation required of the gas chromatography.

The need for rapid temperature programming of miniature chromatographic analysis instrumentation may be accomplished by several design techniques. For example, as described in U.S. Pat. No. 5,014,541, the standard gas chromatography oven is replaced by a tubular heat conductor support on which the gas chromatography column is wound. A heating element within the tubular support is used for temperature programming. In another technique, described in U.S. Pat. No. 3,159,996 a glass tube with three parallel bores and sufficient length to contain a heater wire is provided. A resistance thermometer wire (temperature sensor), with the remaining bore coated on the inside functions as a gas chromatography column. As described in U.S. Pat. No. 5,005,399, a thin film coated capillary gas chromatography column is wound on a mandrill consisting of an insulating material. Electrical current passed through the thin film surrounding the gas chromatography column is used to resistively heat the column.

As described in U.S. Pat. Nos. 5,782,964; 6,209,386; and 6,217,829, gas chromatography systems include a capillary gas chromatography column member is provided which contains a chemical sample to be analyzed, a heating mechanism which extends through the length of the capillary gas chromatography column member, and a temperature sensing mechanism for measuring the temperature of the capillary gas chromatography column member which is mounted adjacent to the column member and are bound together into the gas chromatography system. The gas chromatography systems are placed into a gas chromatography containing the column through which chemical samples are passed and thereby separated.

The ability to readily use these commercially available gas chromatography column technologies in small portable gas chromatography instruments (modules) is desirable for the practical realization of similar analytical capabilities in portable or small gas chromatography instruments.

A number of different technologies have been developed as alternatives to standard air circulation ovens for temperature control in gas chromatography. These technologies have sought to achieve faster GC column heating rates (i.e., fast temperature programming, especially at elevated temperatures), smaller instrument sizes, reduced power consumption, etc. A straightforward approach to working with injectors and detectors in existing GC ovens is to place a heating device directly within the oven to apply local temperature control of the column between its connections to the injector and detector within the GC oven.

Using this approach, resistive heating technology for direct heating of a capillary GC column has been packaged for use in a standard GC oven commercially provided by Thermedics Detection, Inc. (Woburn, Mass.). Thermedics Detection, Inc. has developed a "retrofit" GC system in which a column module is placed within the GC oven, coupled between the detector and injector connection ports, and is remotely controlled by an electronics package separate from the GC instrument. Such a direct approach allows the Thermedics Detection, Inc. system to utilize the fast column heating technology in conjunction with existing sample preparation/injection technique, as well as detection hardware without any changes thereto. Further, data acquisition, analysis and management software that commercially exists may be used in such a system.

In an alternative approach, designed by MT Systems (as described in U.S. Pat. No. 6,093,921), a microwave heated capillary column is placed in a small microwave cavity within the laboratory GC oven to achieve a retrofit GC system for faster temperature programming. This microwave cavity similarly heats most of the columns spanning from the injector to the detector in the oven and is remotely powered by an electronics package separate from the GC instrument.

One of the technical challenges, however, in integrating auxiliary column heating technology into an air circulation GC oven, is the prevention of "cold spots" along the GC column between the injector and detector ports. In the practice of temperature programmed GC, the increased temperature selectively passes compounds having specific boiling points through the column to effectively separate compounds having a wide range of boiling points as known to those skilled in the art. Any "cold spots" in the sample path slow or effectively halt the transit of the sample vapor through the column, thus resulting in delay of the analysis along with degradation or complete loss of detection of the higher boiling point component from a sample injected for analysis.

The injectors and detectors of laboratory GC instruments generally have their own temperature control independent of the oven temperature. The injector/detector's temperatures are typically set close to the maximum analysis temperature required to insure that the samples are vaporized quickly and propagate through the GC column without experiencing "cold spots" at either the injector or detector areas.

While it is standard to set both of these components to operate isothermally at an elevated temperature, chromatographers and instrument designers have found that the GC column attachments to both the injector and detector which descend down into the oven are poorly heated when the oven is not heated. In practice, much of the heating of the injector's and detector's extensions into the oven are accomplished by the air circulation oven rather than the heaters built into the bodies of the devices external to the oven.

Temperatures as low as 80° C. have been measured within the column attachment portion of detectors (extending inside the oven) whereas the portions extended into the oven near the oven wall were heated to 350° C. using standard heaters built into the detector.

Similar to the approaches used by Thermedics Detection, Inc., and MT Systems, Applicants of the present invention perform a direct attachment of a resistance wire heated GC column assembly to the injector and detector within the GC oven in order to eliminate the problem of the "cold spots" at the internal portion of the injector and detector.

In order to solve the problems associated with poorly heated detector and injector ports, the Applicants of the present invention, as well as Thermedics Detection, Inc. and MT Systems, have developed specific hardware for GC systems and added heating zones to the design. For example, the Applicants of the present invention have built supplemental heating enclosures that were insulated and could be opened in order to allow connections to be made. Prior art systems put insulation around the injector and detector ports and fed their connections up into the heated area with a less modular approach.

As shown in FIG. 1, with reference to the prior art, a GC module 10 is placed inside the oven 12. The electronic heater control 14 placed outside the oven 12 is coupled to GC module 10 for controlling the temperature thereof. The ends of the GC column, such as the GC column ends 16 and 18 extend from the GC module 10 to the injector port 20 and to the detector port 22. Supplemental heater zones 24 and 26 heated isothermally by means of electronic heater control connections 28 and 30 are arranged between the GC module 10 and the injector and detector ports, 20 and 22 respectively.

Application of heat to the regions of the detector and the injector ports internally of the oven has resolved the problem and provided chromatography results over the full range of expected boiling points. However, the direct approach of placing the GC module 10 within the oven and providing supplemental heaters which could alleviate the heating shortcomings of the detector and injector ports, have caused the following problems:

(a) Need for Disrupting the Normal Operation of the GC System.

Since the GC module 10 cools with high efficiency, it is difficult to heat this device to high temperatures in the presence of circulating cool air in an unheated air-circulation GC oven. It is therefore necessary to prevent a large fan positioned in the back of the oven (typical for standard GC ovens) from operating while the GC module is being heated. Disconnection of the fan from the GC circuits, on the other hand, can lead to overheating of the GC module due to the buildup of heat within the oven. Additionally, the circuits of many GC instruments do not operate with the fan disconnected for safety reasons. Thus both the fan and the oven heaters may require disconnection. However, non-operation of the oven results in temperature control errors as the built-in temperature sensors report a temperature control failure. This may shut down the electronics of major systems of the GC instrument.

To further defeat the GC oven's temperature sensor, typically a platinum RTD, the sensor can be disconnected and bypassed with a fixed resistor. By using a low temperature coefficient resistor, drift may be minimized and the GC instrument may be programmed to "operate" isothermally at a temperature equivalent to this resistor.

However, the need to interfere with the circuitry and operation of the GC instrument is a concern as this potentially voids manufacturer's warranties and leads to damage of the instruments if not properly accomplished. Further, this provides a significant obstacle to ease of use requiring the user to correctly dismantle the GC instrument and disable or bypass these components.

(b) The Generation of a Significant Heat Load in the GC Oven Making it Difficult to Cool.

The heating of the GC module 10, the injector body 20, the detector body 22, and especially the supplemental heaters 24, 26 of FIG. 1, together generate a large heat load within the confines of the GC oven 12. This makes it difficult to cool the device to moderate starting temperatures in the neighborhood of ambient temperatures (e.g., 30–40° C.). Prior art systems approached this problem by temperature programming the oven over a limited range of temperature while the GC column is (e.g., 40–70° C.) effectively absorbing the heat given off by the GC column while maintaining a temperature control of the oven. This constant cooling by the fan in the relatively cooler oven, however, may potentially interfere with the local heating of the GC column, especially as the local GC column temperatures greatly exceed the air circulation oven temperature. This requires the GC column heating device to be operated with much lower thermal efficiency and possible degradation of its ability to properly control temperatures at higher operating temperatures. Further, the oven starting temperature must be re-established before another analysis can begin.

(c) Free Column Ends for Connections are not Always Desirable.

For certain applications requiring robustness of the components, it is desirable to have the fragile column ends 16, 18 terminate in rigid connectors 32, 34 on the module 10. Without such connectors, the fragile column ends are susceptible to damage. If either of these ends are broken or trimmed to a length too short to make the required connections the integrity of the module 10 is compromised. If a rigid connector is used such as a "union" designed for capillary chromatography is used, it must also be heated. Chromatography unions are typically steel and very massive compared to the column itself and are difficult to heat compared to the GC column which is integrated with fine, temperature-controlled heating wire described in previous paragraphs with regard to U.S. Pat. Nos. 6,217,829; 6,209,386; 5,782,964.

For this reason, a supplemental heating system for the injector and detector in the oven would likely need to also heat these unions further increasing their size and complexity. If free ends 16, 18 of the column are alternatively used, then utmost care is required to avoid breakage during the simultaneous insertion of the free column ends into the injector 20 and detector 30 (especially through the supplemental heating means 24, 26).

(d) Conventional Column Connections are Very Awkward With Minimum Size Supplemental Heaters.

Injectors and detectors are both designed for the column to be manually inserted oftentimes to specific distances. Free ends 16, 18, as part of the GC module 10, are difficult to work with and are likely to result in breakage. If the GC column is modular with connectors 32, 34, then shorter pieces of capillary column may be connected between the injector 20 or detector 22 and the module 10 through the supplemental heaters 24, 26. To minimize the power dissipation, these heaters must have minimum surface areas and should be insulated, while having a span from the detector or injector ports to the module. It has been found difficult to heat distances of 3 to 4 inches from each of these injector/detector ports 20, 22 to the module 10 to temperatures of 300–350° C. without a large heat load being introduced to the oven. If these are made minimal in size, in order to reduce heat dissipation and power consumption, it becomes increasingly difficult to manipulate and thread the GC column through these heaters without breakage of the fragile capillary.

Further, the required thickness for insulation of 0.5–1.0 inch or more reduces the area available within the oven and further limits the space available for handling and threading the column connection pieces into the injector, detector and module connectors. The approach taken by prior art systems require connections that can be very awkward, delicate, and prone to difficulties with "cold spots" or uneven heating.

(e) Difficult to Trim Back Column Connection to Injector.

Many GC analyses require the injection of contaminated samples which contain materials and possibly particulates which degrade the chromatography performance of the entire column. These materials typically do not migrate far down the column, but instead contaminate the coating inside the column for a short distance from the injector. Certain common analysis methods for semi-volatile compounds are prone to such contamination and the GC separation performance is typically regained by trimming back a length of the GC column and reconnection to the injector. While such a "column cutback" approach is possible with GC modules by replacing the column length used to connect the module to the injector, such a replacement within the confines of the insulated supplemental heater system is difficult compared to cutting and reconnecting a column within the large and easily accessible space of a standard GC oven.

(f) Different Designs Required for Every Possible Injector and Detector Geometry.

Since GC ovens often have multiple openings that may be used for injectors or detectors, many different physical placements of these components are possible. This includes detectors such as mass spectrometers which often enter the oven from a side of the oven. The need to make supplemental heated zones which can accommodate GC column modules then requires many different geometries or imposes difficult flexibility requirements on the mechanical designs. This can result in an impractical number of models or design variations.

Thus, it would be highly desirable in the field of chromatography to have a gas chromatography system free of the aforesaid shortcomings of designs of the prior art.

SUMMARY OF THE INVENTION

It is therefore an object of the present invention to provide a gas chromatography system employing gas chromatography column combined with heating elements in a single portable module which is replaceably integratable with a door of the gas chromatography oven.

It is a further object of the present invention to change a design of the conventional gas chromatography oven by replacing a door (or any wall thereof) with a novel door (or a wall) which is provided with a module receiving slot in which the column module may be easily secured to extend external the oven and wherein free column ends projecting from the gas chromatography column module to the injector and detector port inside the oven are heated isothermally.

It is another object of the present invention to change the fabrication of existing gas chromatography systems by replacing a conventional door with a novel door construction which allows it to be integrated with the column module with no need to interfere with a fan, heater, or the temperature sensors, and with no risk of misconnections or damaging the electronics of the existing GC system.

It is a still further object of the present invention to provide a gas chromatography system where the heat generated by the modules is exterior to the oven, while the oven is heated isothermally to heat the module connections and extensions of the detector and injector into the oven. Thus, not requiring cool down of the oven for each analysis, since the module contains most of the GC column length outside the oven which is rapidly heated and cooled.

A further object of the present invention is to provide a gas chromatography system where it is possible to combine in a single system both fast temperature cycles applied to the low thermal mass component of the module outside of the oven and heating of the larger thermal mass components within the oven while maintaining an interface between the components inside the oven and outside the oven in which the oven heat does not significantly externally conduct and interfere with the temperature cycling of the module components.

It is another object of the present invention to provide a simple replacement of column modules as well as easy access to the injector and detector ports for connection thereof to the capillary connectors of the module.

A further object of the present invention is to provide a gas chromatography system permitting the inclusion of multiple GC column modules, thereby providing the opportunity for more advanced GC analysis on two (or more) different GC columns and then detecting the results with a pair (or more) of detectors. In this manner, multi-column analyses may be accomplished where not only multiple temperature programs can be conducted but the plurality of modules may perform sophisticated temperature programs. For example, the exterior air cooled modules may perform multi-segment temperature programs which contain negative ramps, as well as positive ramps for advanced applications of gas chromatography analysis. The independent temperature programming of multiple modules also allows the sequential operation of columns in series or in combination with valves and individual detectors.

It is still another object of the present invention to provide a column module for the gas chromatography system which includes a column module portion combinable with a transfer line module portion which may be inserted into the module receiving openings provided in the oven door either simultaneously or in a predetermined order.

According to the teachings of the present invention, a gas chromatography (GC) system includes a GC oven having an oven cavity enveloped by walls and a door wherein a door has up to four module receiving openings defined therein, and wherein a wall of the oven has openings for injector and detector ports. Up to four GC column modules may be removably secured within the module receiving openings of the oven door for gas chromatography analysis.

Each GC column module comprises:
a module housing formed of a perforated stainless steel,
a capillary column where the main coil is contained within the module housing and free ends extend beyond the walls of the module housing,
a pair of transfer lines each coupled to a respective free end of the main column,
a heater wire positioned adjacent the transfer lines,
a pair of chromatography connectors with each coupled to a respective one of the transfer lines and extending from the GC column module into the oven cavity, and
a mechanism for securing the column modules to the oven door.

The GC system further includes first and second GC column lengths positioned within the oven cavity. The first GC column length extends between a respective gas chromatography connector and the injector port, and the second GC column length extends between another gas chromatography connector on the module and the detector port.

The system further includes a temperature control unit attached to the oven door outside the oven cavity operatively coupled to the heater wire and the transfer line. A heater is positioned within the oven cavity for heating the same isothermally.

The subject oven door of a new design replaces the conventional oven door by means of hinges positioned at one side edge of the door and a latch mechanism positioned at another side edge of the oven door for hermetically closing the oven.

The oven door constitutes a multi-layer structure providing for a sufficient thermal isolation between the oven cavity and the external surroundings. Particularly, the oven door includes an inner plate having feed through holes for projection of the module's chromatography connectors therethrough, a layer of insulating material attached to the inner plate, an insulation retaining plate attached to the layer of insulation material, an aluminum insulation frame attached to the insulation retaining plate, and an outer door attached to the aluminum insulation frame.

Each of the layers of the oven door has slots defined therein in aligned disposition, thus defining the module receiving openings of the oven door for receiving the face end of the module therein.

Preferably, the temperature control unit includes heating control circuits, electrical connections to the GC modules, a microprocessor and a user interface.

Positioned in close proximity to each module is a cooling fan attached to the oven door externally the oven cavity.

The GC column module is envisioned in two alternative designs. One design includes:

a module base plate,
a module cover attached to the module base plate, thus forming a module housing,
a capillary column in the module housing,
a pair of transfer lines,
a module face plate attached to the module housing at one end through a face plate insulation (the face plate insulation and the face plate both have openings for projecting the free ends of the capillary column therethrough), and
a pair of module clamps attached to the module face plate in alignment with the openings.

Each module clamp has an aperture provided for projection therethrough of a respective one of the chromatography columns.

Each transfer line is a thin walled tube formed of steel or like material heated by resistance wire and sleeving the free ends of the main capillary column. Each transfer line is heat compensated by reducing the number of heater wire windings around the transfer line along the length of the transfer lines entering into the oven cavity.

In an alternative embodiment, each GC column module includes a column module having the module housing containing the main coil. A transfer line module is included which comprises a transfer line housing, a pair of tubes secured to and extending through the transfer line housing for sleeving the free ends of the capillary column, a pair of bars extending from the transfer line housing at a face end thereof in proximity to the pair of tubes, and a mechanism for securing the transfer line module to the column module. In order to integrate the GC module to the oven door, the module of this embodiment may be either assembled before inserting the module into the modular receiving opening in the oven door or the transfer line module may be secured to the module receiving opening and the column module can be further coupled to the transfer line module.

These and other features and advantages of the subject invention will be more fully understood from the following detailed description of the accompanying Drawings.

DESCRIPTION OF THE PREFERRED EMBODIMENTS

The basic principles of the gas chromatography analysis include introducing a sample through the injection port of the gas chromatography system into a stream of carrier medium. This supplies the sample to be examined into a capillary column (constructed in the form of a helix of tubing containing chemicals that cause some of the constituents of the sample to elute at different times). The capillary column is attached to the injection port and supplied from the column to the detector for producing a signal indicative of the concentration of the constituents being eluted. The column is exposed to programmable temperature control in order to increase the temperature of the column from an initial minimum value to a maximum final value to allow the compounds to be analyzed with a higher boiling temperature point. Since the column is the component of the GC system in which the sample to be analyzed is separated it is commonly called a separation column.

Figure 1:
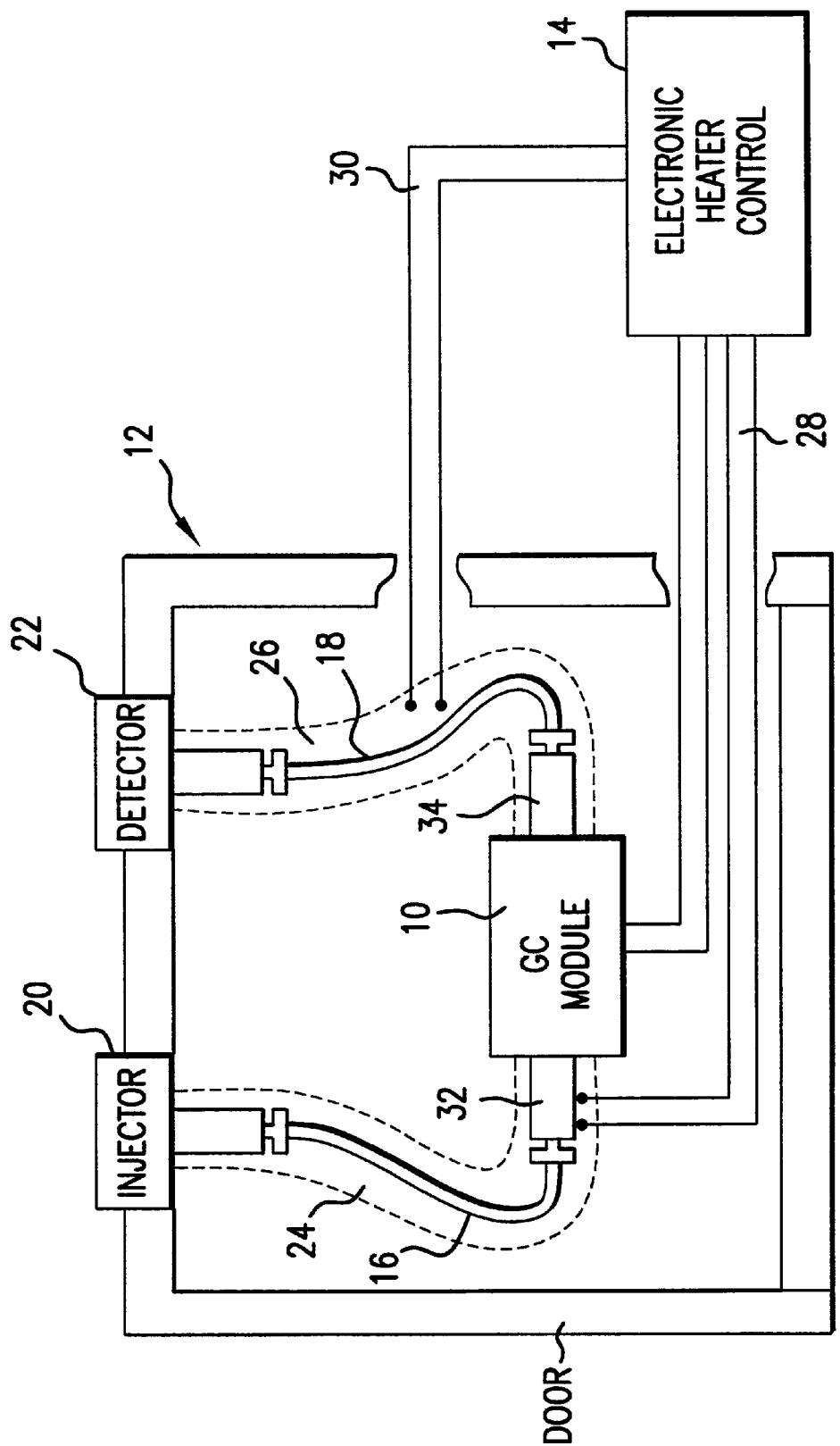
FIG. 1 schematically depicts the gas chromatography system of the prior art with the GC module inside the oven.
Figure 2:
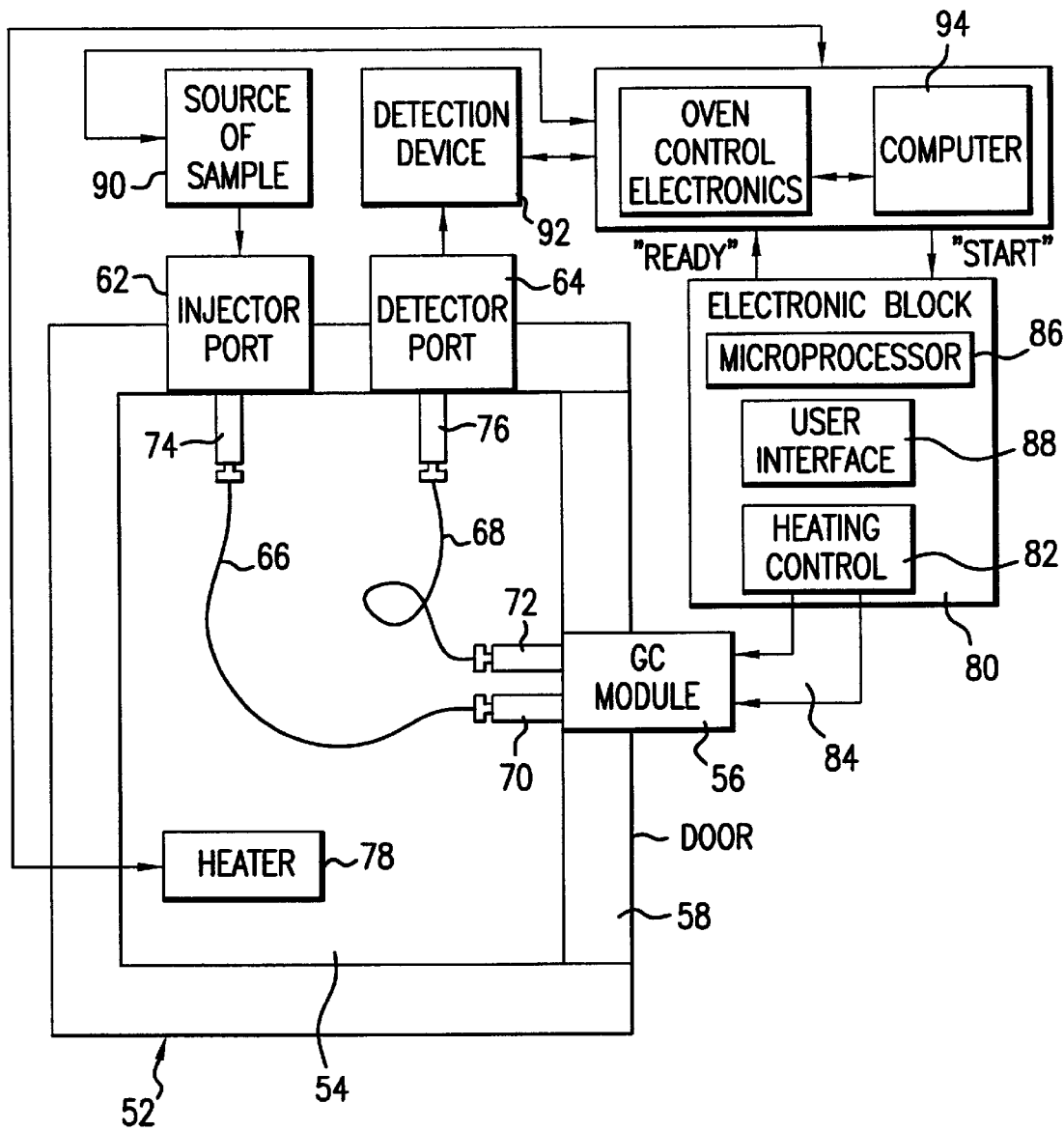
FIG. 2 illustrates schematically the concept of the present invention, wherein the GC module is incorporated into the door (or a wall) of the GC oven.

Referring to FIG. 2, a GC system 50 comprises a GC oven 52 which includes an oven cavity 54 surrounded by oven walls and an oven door. These are hermetically closed and provide sufficient thermal insulation between the oven cavity and the external environment of the GC oven. A GC module 56, which will be described in detail in further paragraphs, is integratable with any of the walls of the GC oven, however, it is preferably attached to the oven door 58 for which purpose an oven door of a conventional air circulating GC oven is replaced with oven door 58 of the present invention adapted specifically for attaching the GC modules 56 (from one to four GC modules) thereto.

A wall 60 which may be any wall of the GC oven but preferably the closest to the oven door 58, has two openings defined therein for providing injector port 62 and detector port 64 of the gas chromatography system 50. A pair of capillary column lengths 66 and 68 extend between chromatography connectors 70 and 72 (extending from the module 56 into the oven cavity) to the chromatography connectors, one of which is the injector connector 74 and another is a detector connector 76 which extend into the oven cavity 54. "Phaseless" capillary as often sold for use in so-called "guard" columns or transfer lines is usually preferred for column lengths 66 and 68. The column lengths 66 and 68, as well as chromatography connectors 70, 72 of the module, and injector and detector connectors 74 and 76 are exposed to the thermal conditions created within the oven cavity 54 by a heater 78.

An electronic block 80 is positioned at the oven door 58 outside the oven 52. The electronic block contains heating control circuits 82, electrical connections to the module 84, a motherboard with a microprocessor 86, and a user interface 88. The microprocessor 86 and the user interface 88 may be parts of a computer 94 positioned within the electronic block 80 or separate therefrom. The electronic block can send and receive signals (e.g., READY or START signals) in communication with the microprocessor controlling the GC oven or a remote computer controlling the GC oven or related sample injection instrumentation. The electronic block can be integrated with a wall of the GC oven such as the door, or be packaged separately from the oven.

The injector port 62 is coupled to the source of a sample 90 for injecting the compound to be analyzed into the chromatography column. The detector port is coupled to a detection device 92. Both the source of sample 90 and the detector 92 are typically coupled to the control electronics of the gas chromatograph. The injection device, detection device 92, the oven control electronics as well as the electronics packages associated therewith, may assume a variety of circuits and structural configurations well known in the art. These provide proper chemical samples to the gas chromatography system 50 as well as appropriate heating and control mechanisms associated with the analysis. The detector device 92 can be any of the known detectors, such as flame ionization detector, or a mass spectrometer.

A sample injection technique by which the sample is injected into the system from the source of sample 90 may utilize a sample injection technique with a pressurized carrier gas, in which the carrier gas is supplied to the injection port 62 from the source of sample 90 through an appropriate valve (not shown) which serves to control the pressure of the carrier gas in the gas chromatograph system 50. The sample can be considered as being injected using any conventional technique known to those skilled in the art.

Figure 3:
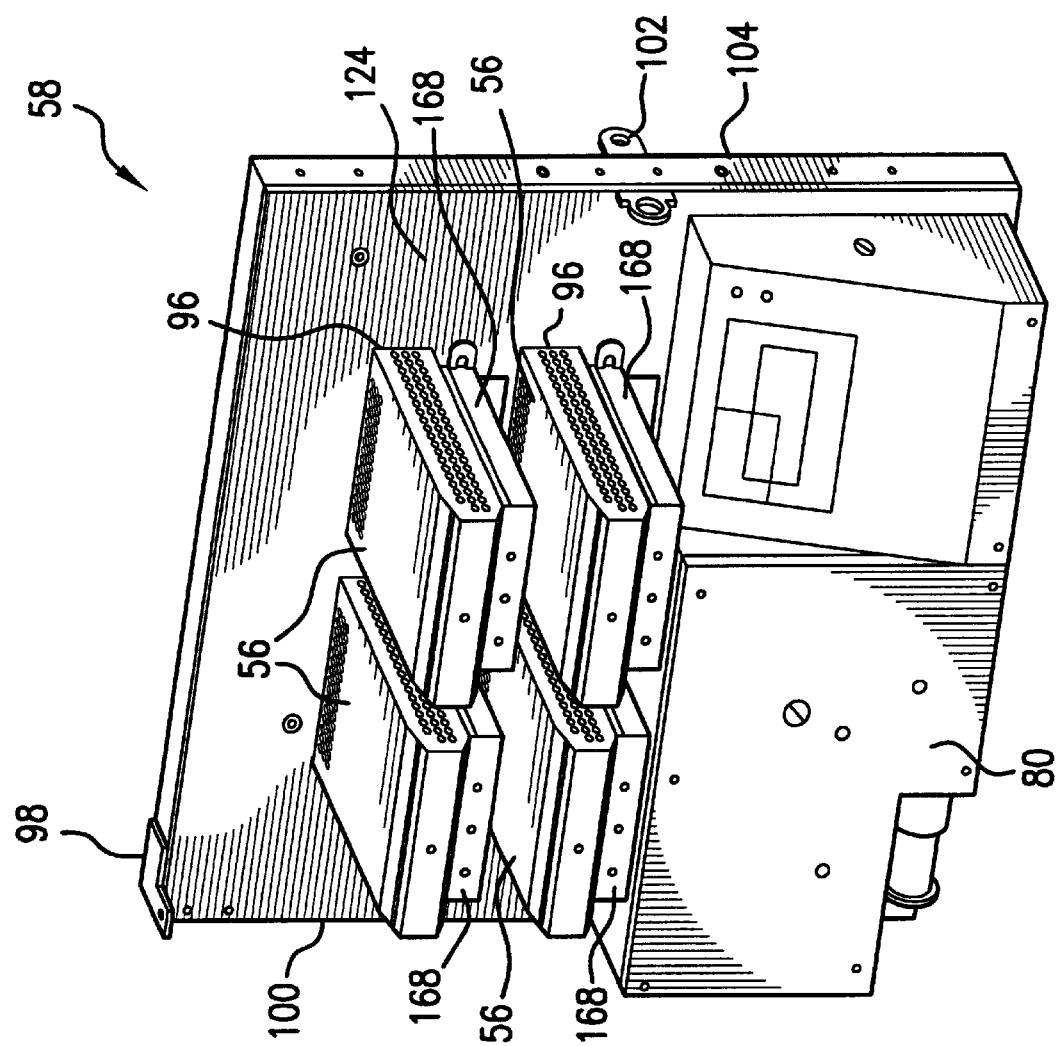
FIG. 3 is an illustration of a door of the present invention for the GC oven carrying four GC column modules thereon along with the control electronics.
Figure 4:
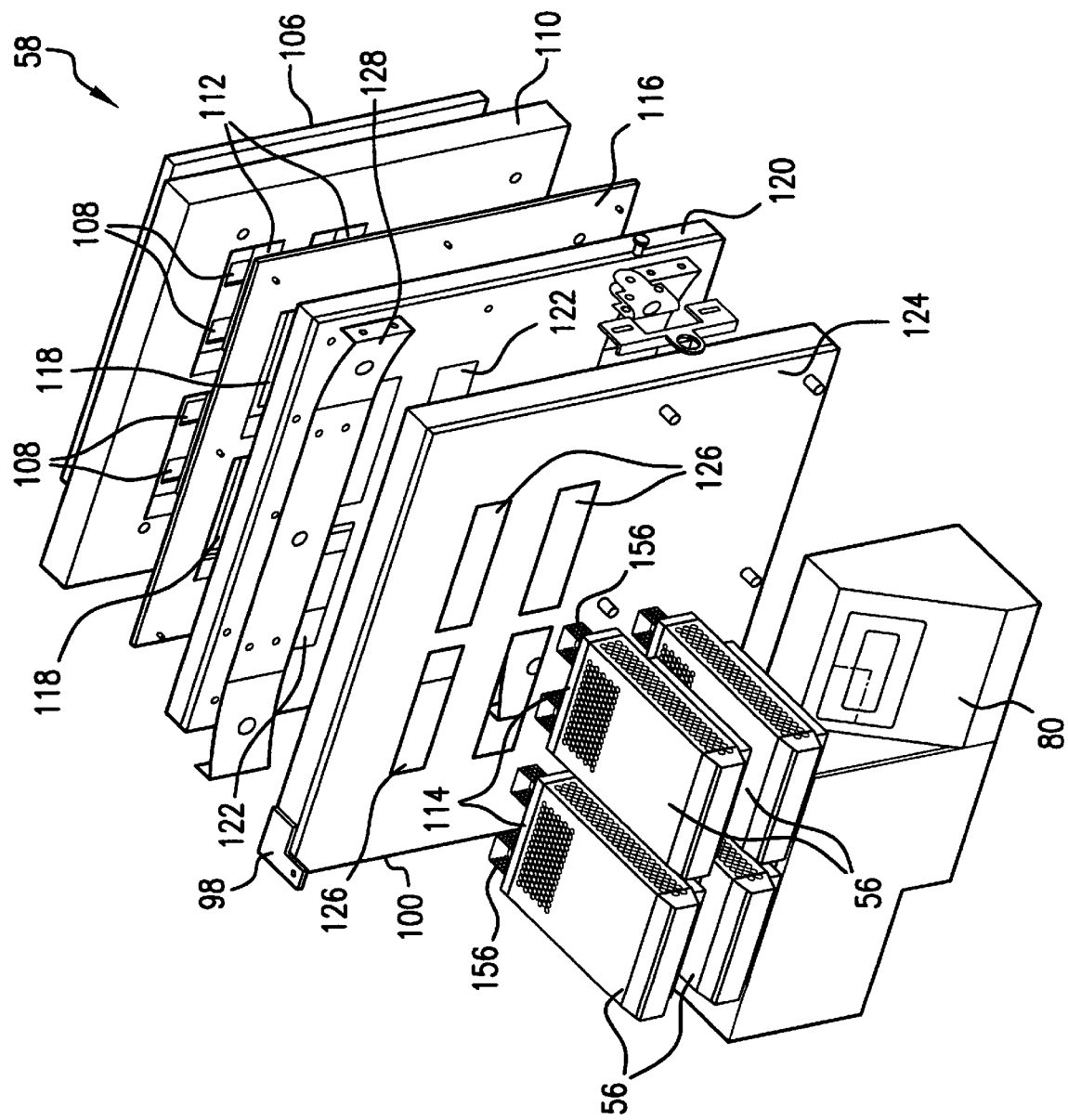
FIG. 4 is an exploded view of the door of the present invention with the GC column modules removed from the door, and showing the control electronics disassembled from the door.

Referring to FIGS. 3 and 4, the oven door 58 includes up to four module receiving openings 96 formed in the door 58 at predetermined positions. The door 58 is designed to be a replacing element for any conventional GC oven, for instance, as a replacement door for the Hewlett Packard 5890 series gas chromatograph, and others having similar doors. Hinges 98 located at the left side edge 100 of the door 58 and the latch mechanism 102 on the right side edge 104 of the door provide for a simple replacement mechanism. The door 58 includes the following parts:

an inner plate 106 (contiguous with the oven cavity 54) having feedthrough holes 108 for the chromatography connectors 70 and 72 projecting from each module 56;

a layer of insulation 110 having four rectangular slots 112 for accommodating the face end 114 of the module 56 therein;

an insulation retaining plate 116 having four openings 118 for the module face end 114 projecting therethrough;

an aluminum insulation frame 120 having slots 122 formed therein, and an outer door 124 having four openings 126 positioned in alignment with the slots 122 in the aluminum insulation frame 120, openings 118 in the insulation retaining plate 116, and rectangular slots 112 in the layer of insulation 110.

All layers of the oven door 58 are secured each to the other to form a multi-layer structure having high temperature insulation properties. The hinges 98 and the latch mechanism 102 are preferably positioned on the outer door 124. The inner door which includes the inner plate 106, the layer of insulation 110, insulation retaining plate 116, and aluminum insulation frame 120 is attached to the outer door 124 by a pair of leaf springs 128, best shown in FIG. 4. An insulating fabric (not shown) is positioned between the inner plate 106 and the layer of insulation 110, wraps around the layer of insulation 110, and seals the insulation retaining plate 116 and aluminum insulation frame 120 to form a fabric gasket for the oven door around the edges of the layer of insulation 110.

The electronic block 80 is secured to the lower front of the door 58 to provide a four-channel control heating of the modules 56 as well as a user interface.

Figure 5:
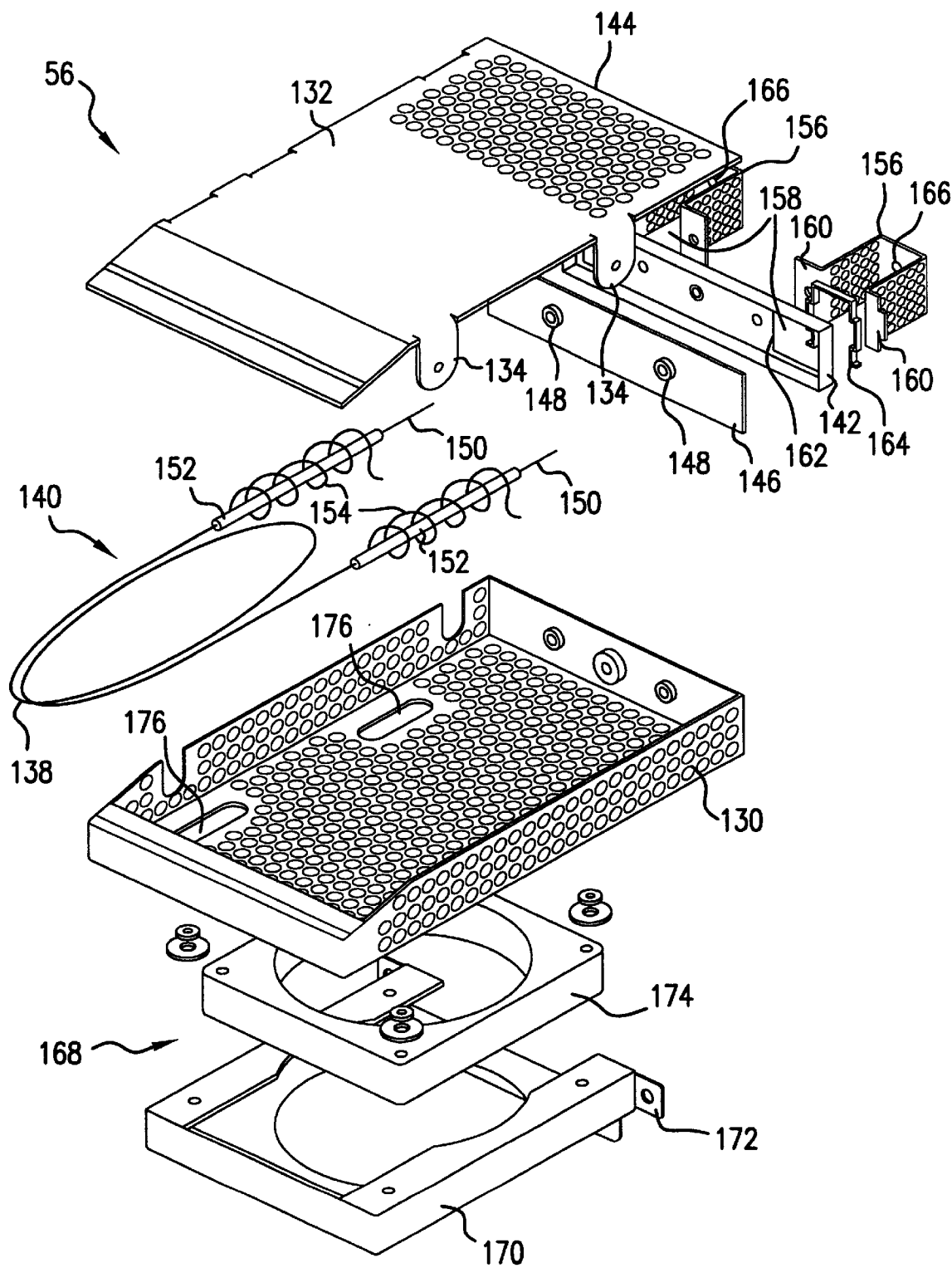
FIG. 5 is an exploded view of the GC column module of the present invention.
Figure 6:
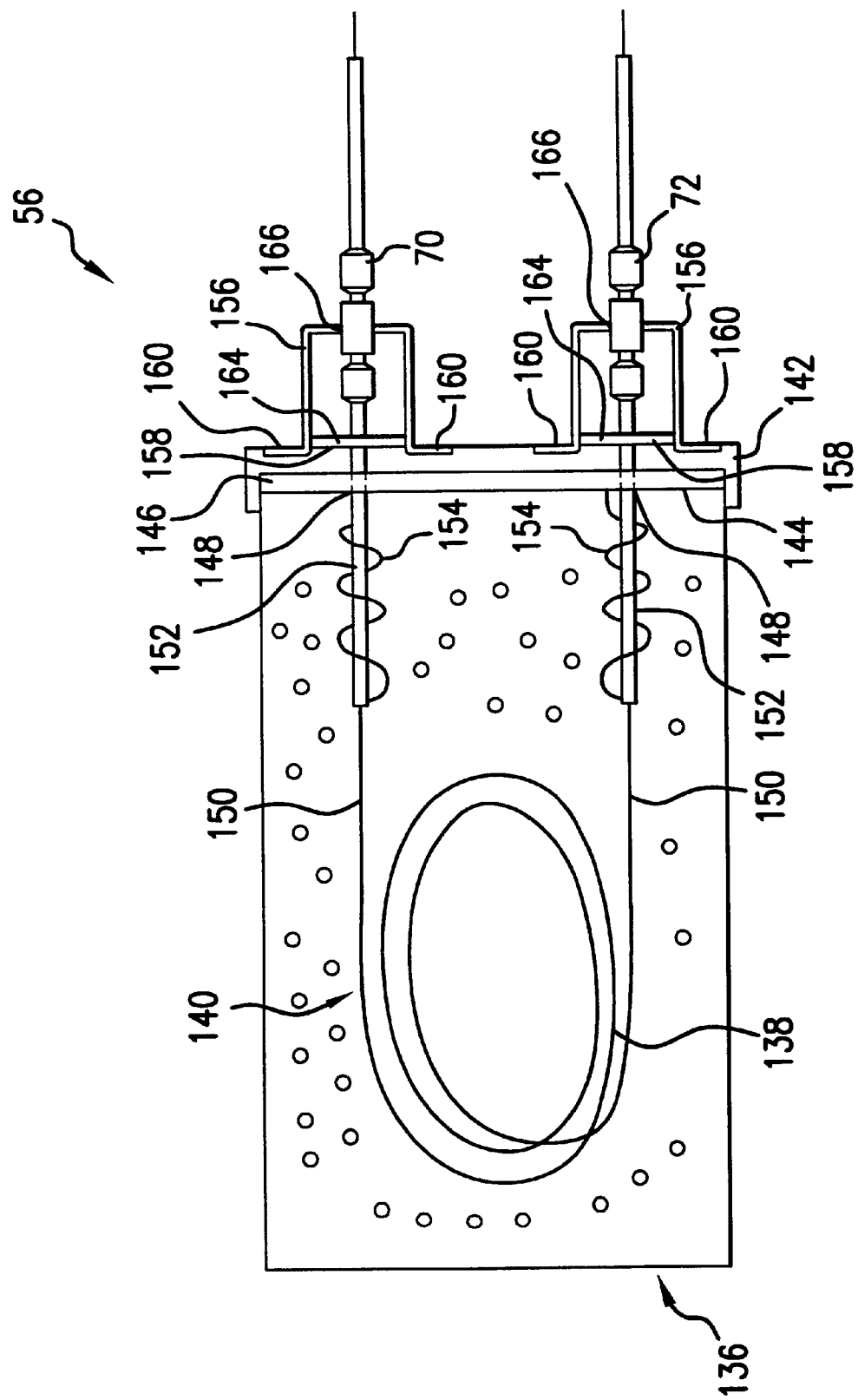
FIG. 6 is a top view of the assembled GC column module of the present invention.

Referring to FIGS. 5 and 6, the module 56 includes a module base 130, a module cover 132 having tabs 134 extending from the edges of the module cover 132 for securement to the module base 130 to form a module housing 136 in which a main column 138 of the capillary column 140 is contained. The module housing 136 further includes a face plate 142 secured to the face end 144 of the module housing 136 through a face plate insulation 146. Both the face plate 142 and the face plate insulation 146 have openings 148 defined therein for allowing free ends 150 of the capillary column 140 to project therethrough.

Each module 56 further contains a pair of wire heated tubes 152 (transfer lines) which sleeve the free ends 150 of the capillary column 140 and which extend through the insulation barrier of the oven door 58 into the oven cavity 54. Each tube 152 is formed of a thin walled steel of relatively low thermal conductivity which is wound with a heater wire 154 controlled by the heating control circuits 82 of the electronic block 80. The heater wire 154 is contained within the module housing 136 and terminates near the insulation barrier of the face plate insulation 146.

The wire heated tube 152 along with the free ends 144 of the capillary column 140 project to the chromatography connectors 70 and 72 which extend into the oven cavity 54.

Two module clamps 156 are attached to the face plate 142 to hold the tubes 152, as well as chromatography connectors 70 and 72 in proper position. In order to attach the clamp 156 to the face plate 142, the face plate 142 has two openings 158. To secure each module clamp 156 to the face plate 142, the resilient module clamp 156 is squeezed and after projection into the opening 158 is released in order that the tabs 160 of the module clamps 156 engage the edges 162 of the openings 158 thus securing the module clamps in position.

Each of the module clamps 156 is provided with a clamp spring 164 which embraces a wire heated tube 152 thus holding it in position. Each module clamp 156 has an aperture 166 through which the gas chromatography connectors 70 and 72 project and are supported in proper position.

As best shown in FIG. 6, the bare fused silica column, specifically the free end 150, emerges from the tube 152 and is coupled directly to the chromatography connector (70 or 72) with a bulk head mounted to the supporting module clamp 156.

The module clamp 156 is formed of perforated stainless steel so that in addition to the low mass clamp spring 164 it minimizes thermal conduction to the interface between the module 56 and the oven cavity 54 for reducing the cooling of the oven cavity in proximity to the oven periphery.

Referring again to FIGS. 3–5, a fan module 168 is positioned in close proximity to each module 56. The fan module 168 comprises a fan bracket 170 which is attached to the oven door 58 by flanges 172 and fasteners (not shown). A cooling fan 174 for accelerated cool down of the module 56 is housed in the fan bracket 170. As best shown in FIG. 5, the module base plate 130 has key hole slots 176, which are located over the fan bracket 170. The module base plate 130 can slide towards the oven where it is attached to the door from the inside using a captive thumbscrew (not shown).

Figure 7:
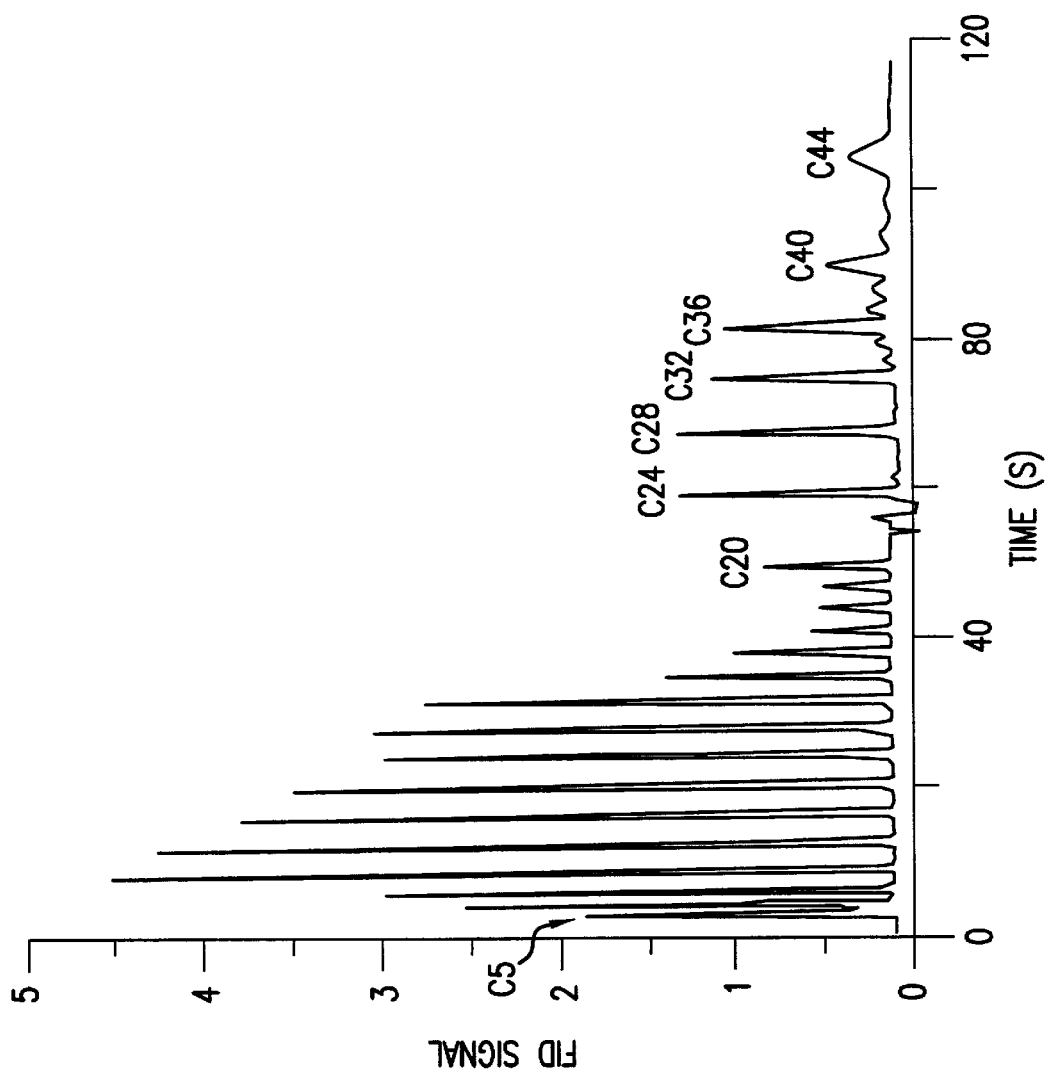
FIG. 7 is a diagram showing some fast high temperature chromatography data obtained with modules of the present invention integrated with a typical GC oven having a Model #HP5890 produced by the Hewlett Packard Corp.

FIG. 7 describes some fast high temperature chromatography data obtained with modules 56 integrated with the door 58 which replaces the conventional door of the HP 5890 gas chromatographer for separating high boiling point mixtures of hydrocarbons. In this separation, the module 56 containing a 5 m×0.32 mm (internal diameter) capillary column having a 0.5 micron film thickness of silicone polymer stationary phase was used with a helium carrier gas flow rate of 20 mL/minute. A test standard mix, SD-006, provided by Separation Systems Inc. (Gulf Breeze, Fla.) is injected using a split injector 90 heated to 350° C. with a split ratio of 10:1. A flame ionization detector 92 operated at 375° C. for detection. The temperature program consisted of the following ramps: 40° C. to 360° C. at 4° C. per second, followed by isothermal operation at 360° C. for 20 seconds. The fan 174 cooled the column down to 40° C. from 360° C. in 60 seconds.

The chromatogram, shown in FIG. 7, illustrates the ability of the GC system 50 of the present invention to separate from pentane C5 (a very low boiling point compound), up through C44, (a high boiling point hydrocarbon) in less than 2 minutes. Analysis cycles much shorter than 3 minutes are readily demonstrated using even faster temperature programming rates, but with some loss of resolution compared to the example shown in FIG. 7. The broadening and increased spacing of the peaks above C32, shown in the chromatogram of FIG. 7, is the result of the temperature program becoming isothermal at 360° C. near the elution of C32.

Figure 8:
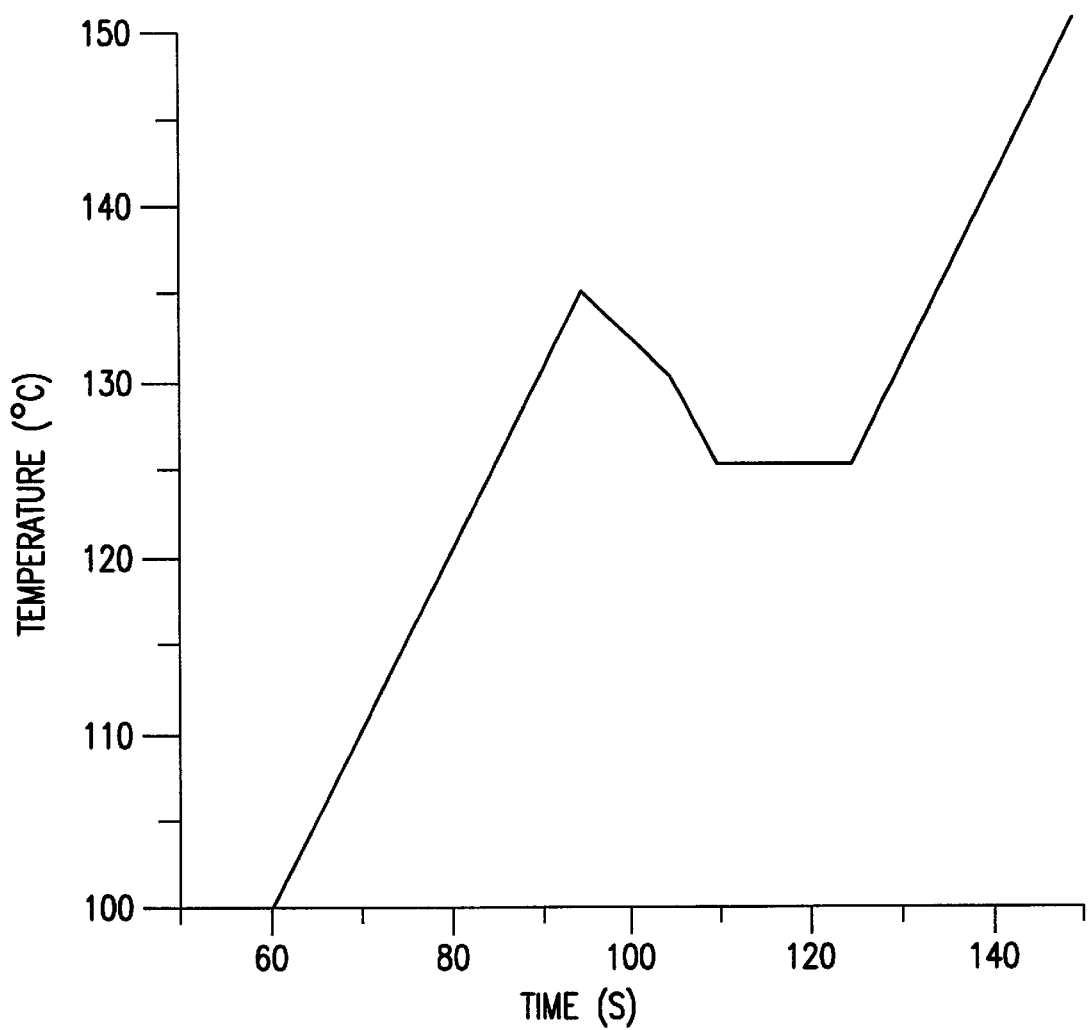
FIG. 8 is a diagram showing a series of temperature programming segments in which two negative ramp segments are included (this temperature program was used with a fast GC separation technique of the present invention of a mixture of components to expand a region of the chromatogram and spread the peaks midway through the separation)

FIG. 8 shows a series of temperature programming segments in which two negative going ramp segments are included. This temperature program was used with a fast GC separation of a mixture of components to expand a region of the chromatogram and spread the peaks midway through the separation. Following the temperature drops and the isothermal region, the temperature programming was resumed at 1° C. per second. The initial temperature programming rate was 1° C. per second up to 135° C. This was followed immediately by two negative going temperature ramp segments: 135° C. to 130° C. at −0.5° C. per second, and 130° to 125° C. at −1.0° C. per second. This shows the ability of the GC system of the present invention with the externally air cooled modules 56 to perform more complex temperature programs for fast separation.

The design of the gas chromatography system 50 of the present invention is capable of very high temperature operation in excess of 450° C. (842° F.). This exceeds the temperature limitations of standard gas chromatography ovens. This high temperature operation places special demands on module design, materials used, conduction/distribution of heat within the modules, and compensation for oven heat in the operation of the module's own heating components. To this end, the design includes the following features:

1. Use of compression fittings of a conventional design which have been selected for their stability at high temperature and their resistance to leakage at high pressure connections under the stresses of high temperature. These fittings are formed of stainless steel, glass coated steel and may include high temperature ferrules for compression fittings.

2. The module 56 is formed entirely of stainless steel and high temperature ceramic fabric 146 (more than 1000° C. temperature stability for the fabric) is placed at the end which interfaces with the oven interior. The use of stainless steel in the module design reduces heat conduction. Further heat conduction reduction near the oven end of the module is provided by extensively perforated material of the module.

3. The resistance wire heated tubes (transfer lines) 152 which are used to sleeve and to control the temperature of the free ends 150 of the capillary column 140 entering and exiting the main coil 138 in the module 56, are compensated for the heat which diffuses and connects from the oven cavity 54 through the module 56.

During elevated temperature operation of the GC oven, a large temperature gradient develops through the insulation surrounding the oven cavity. At 350° C. operation, the gradient may go from 350° C. in the interior of the oven wall to a much reduced temperature at the exterior of the insulation such as 50° C.

In the module receiving opening 96 formed in the oven door 58, where the module 56 penetrates through the insulation of the oven, the module is heated directly by contact with the inner plate 106 of the oven door at its face end 114, and heat is also dissipated from the insulation laterally to the module. While the module is heated by a combination of conduction and convection effects, the air in the module receiving openings also convects some heat from the opening area.

When the temperature gradient within the module receiving opening 94 is measured as a function of the distance from the oven inner plate, it is found that the temperature gradient has lower temperatures than the gradient in the insulation (approximately linear gradient). The transfer lines 152 pass through these gradients connecting the main coil 138 of the GC capillary column 140 in the module to the oven cavity.

Both the main coil 138 and the temperature sensing regions of the transfer lines 152 (near the point where the transfer lines join the main coil), are sufficiently removed from the oven gradient so that they are not adversely heated by the oven internal temperature and can control temperature accurately independent of the oven temperature.

However, if the oven gradient is not compensated in the transfer lines 152, then the ends of the lines passing through the gradient will be overheated by the additional heat contributed by the oven cavity. If the capillary column is operated at the upper operating limit for the coatings in a particular column (e.g., 360° C. for a polyimide-coated fused silica column containing a polydimethylsiloxane stationary phase), the transfer line would need to be heated to approximately 360° C. along its length for the chromatography not to be adversely affected. However, the portion of the transfer line traversing the gradient from the oven may reach temperatures in excess of 430° C. due to the fact that there is additional heat from the oven cavity. For this reason, the number of heater wire windings per inch along the length of the transfer line going toward the oven cavity in the region of the gradient is reduced. The measurements of this gradient (measured in the module with the module's heating off) and the measurements along the width transfer line with and without temperature compensation has shown relatively uniform heating.

Figure 9:
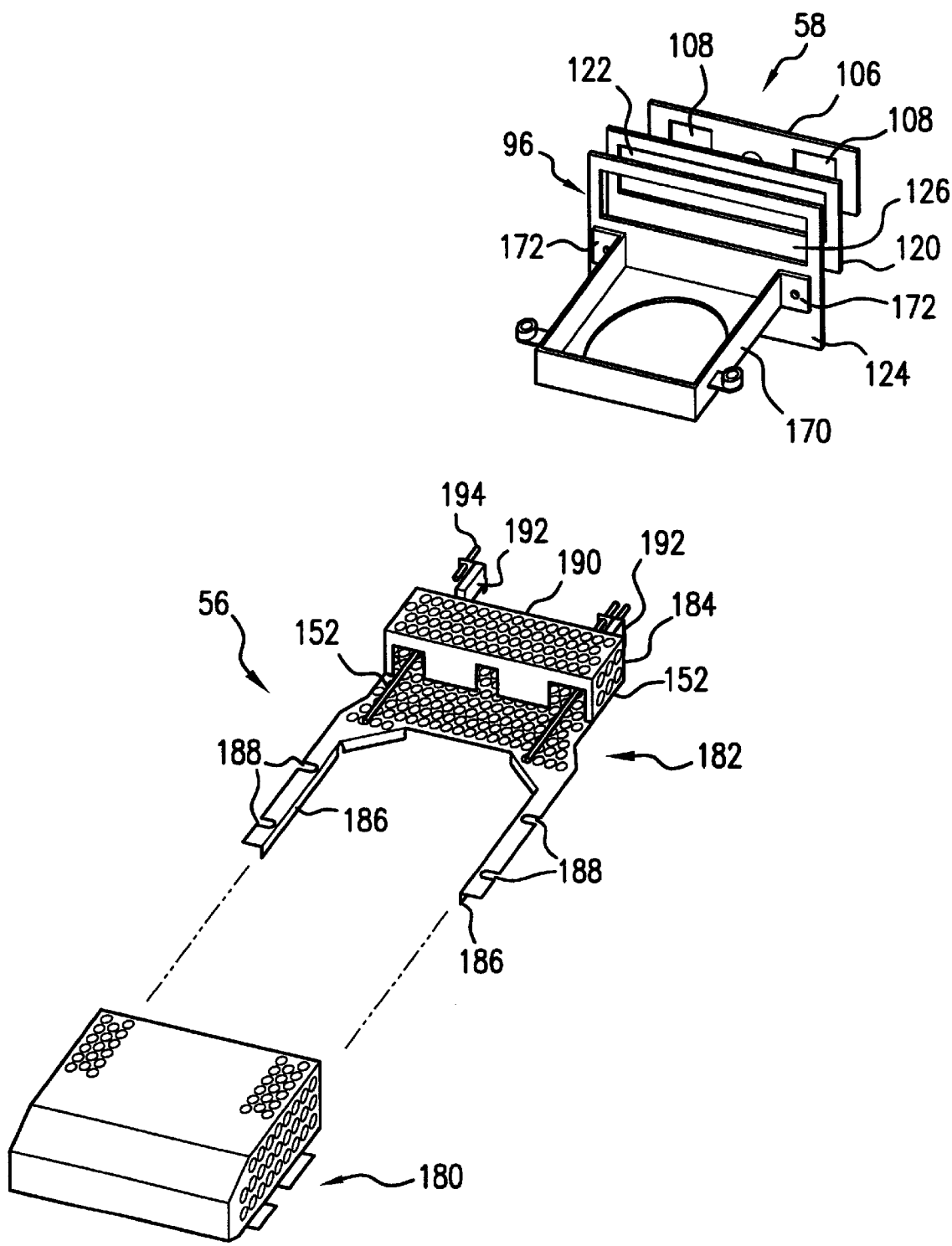
FIG. 9 is an exploded view of the alternative embodiment of the module of the present invention.
Figure 10:
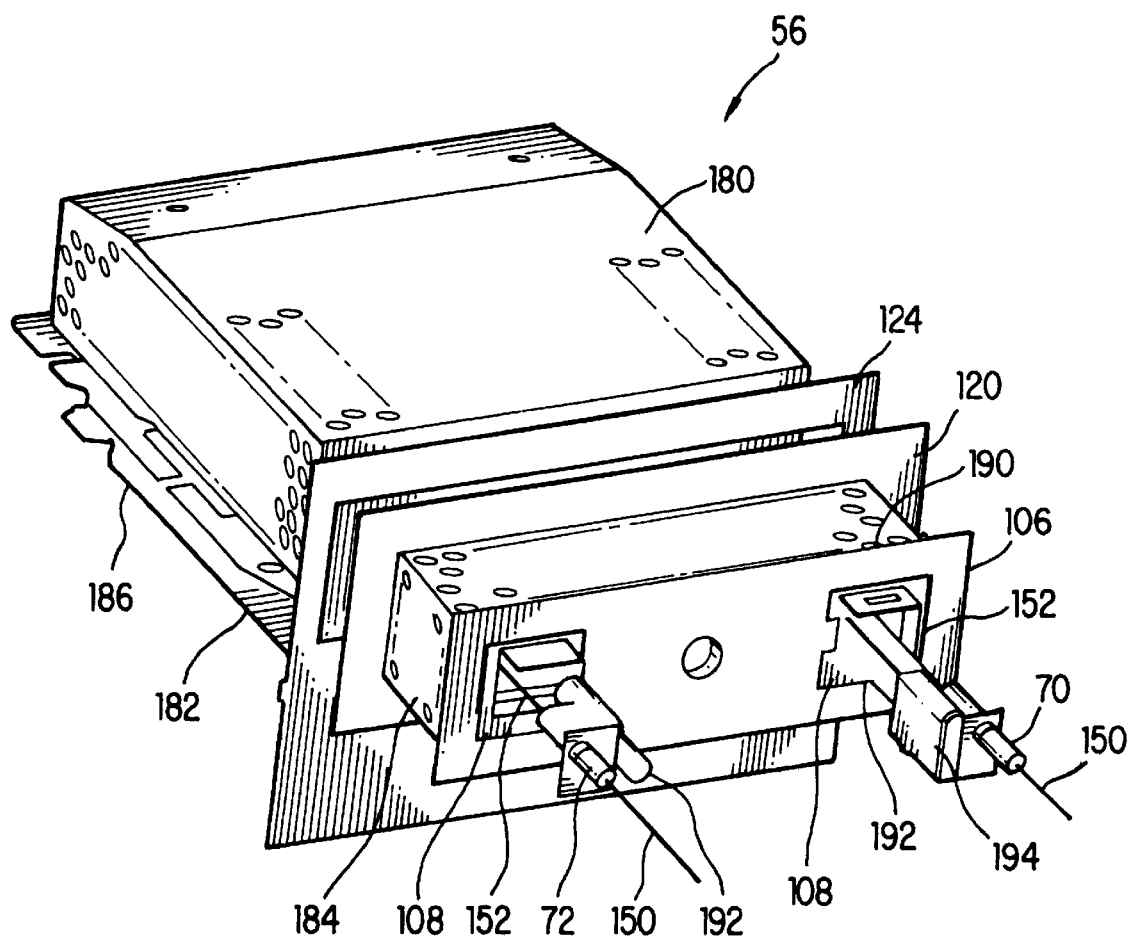
FIG. 10 is a combined module of the present invention inserted into the slot of the oven door of the present invention viewed from the rear side (internal the oven).

Referring now to FIGS. 9–10, showing an alternative embodiment of the module 56 of the present invention, this module includes a column module 180 and a transfer line module 182 which are removably integratable each to the other to form a single module 56 of the present invention. The column module 180, and transfer line module 182 when combined constitute the equivalent to the module shown in FIGS. 5 and 6.

The column module 180 is a column housing formed of a perforated stainless steel in which a main coil 138 is received with free ends 150 of the capillary column 140 extending from the column module 180.

The transfer line module 182 has a perforated steel enclosure 184 containing insulation adjacent to the faceplate 190 where it meets and attaches to the inner plate 106. For very high temperature operation, the insulation enclosure 184 reduces heat transfer from the oven through the openings in the insulation 112, although the temperature gradient through the enclosed insulation 184 is also greater than the gradient in the open air of the module 56 without insulation. Accordingly, the heater windings 154 on the transfer line 152 are adjusted to compensate for the different temperature gradient in the transfer line module to achieve uniform heating of the capillary 150 contained within.

The pair of transfer lines 152 project through the transfer line housing 184 at predetermined locations for sleeving the free ends 150 of the capillary column 140 of the column module 180 when both column module 180 and transfer line module 182 are combined.

In order to secure both modules one to the other, the transfer line module 182 has a pair of flanges 186 extending from the transfer line housing 184 with slots 188 keyed to screw clamps (not shown) to fasten the column module 180 to the transfer line module 182.

On the face side 190 of the transfer line module 182, a pair of bars 192 extend outside of the transfer line insulation enclosure 184 and project into the oven cavity. Brackets 194 are fastened to the bars 192 for sliding therealong. The gas chromatography connectors 70 and 72 of the module are supported by the brackets 194 at predetermined positions along the bars 192. A user may cut the capillary column to a desired length and attach the chromatography connectors 70 and 72 along the bar 192 to complete the module. Optionally, if a chromatographer does not wish to use chromatography connectors 70, 72 of the module (in some types of trace analysis in which the ferrules and connector materials may interfere with the chemical analytes by adsorption or reaction), the column module with free ends long enough to reach the injector and detector ports may be used. Although long free ends at high oven temperatures may cause chemical noise background in detectors (commonly referred to as "column bleed"), this unwanted effect can be eliminated by using columns having integrated "guard" column that is free of the column coatings responsible for bleed.

The module, shown in FIGS. 9 and 10 may be combined external the oven, and the combined module may be inserted into the module receiving opening 96 on the oven door 58. Alternatively, the transfer line module 182 may be first inserted into the module receiving opening 96, and the column module 180 may be attached to it subsequently. The use of the two piece module provides the chromatographer with a simple and less expensive way to change columns without having to replace the transfer lines and components contained in the transfer line module 182. It also provides for the possibility of not using chromatography connectors 70 and 72 in the design as well as to extend free ends of the column directly from the module to the injector and/or detector without the need of adding separate gas chromatography lengths 66 and 68, shown in FIG. 2 which are coupled to the free ends 150 of the main coil by means of chromatography connectors 70 and 72.

By using such a specific arrangement of the gas chromatography system 50, the Applicants of the present invention have achieved the long sought and long desired advantages, such as:

(a) No Need to Disrupt the Normal Operation of the GC.

While the modules could interface through any wall of the GC, in principle, by selecting to interface through the door, the oven door can be easily replaced with a new design which accepts modules. Since most GC instruments have no electronics or special features built into their doors, this replacement is as simple as removing a hinge pin, replacing the door, and reconnecting the hinge pin. There is neither need to interfere with the fan, the heaters, or the temperature sensors of conventional GC systems, nor is there a need to risk misconnections or damaging the electronics of the GC. The novel oven door provides for a simple approach to retrofitting GC modules to existing air-circulation GC instruments.

(b) The Heat Generated by the Modules is Exterior to the Oven and of No Consequence.

Unlike conventional approaches of the prior art, where most of the heat in the designs placing all of the components inside the oven comes from the supplemental heating zones which are operated isothermally at high temperatures (e.g., the maximum temperature of the analysis such as 325–350° C.), in accordance with the present invention, the oven is only heating the module connections and the extensions of the detector and injector into the oven. The oven is not required to cool down and expel all of its heat for each analysis because the module containing most of the GC column length is outside the oven and rapidly heats and cools.

(c) The Module can Easily Terminate in Robust Connectors that are Heated by the Oven.

While free column ends could be inserted into the oven through the door and directly into the injector and detector, the module can also have robust connectors designed specifically for capillary chromatography connections that project into the oven and are effectively heated by the oven air. This is an important consideration because chromatography connectors are bulky compared to the capillary column itself and are more difficult to heat and cool quickly. Even miniature chromatography unions, such as the "mini-unions" made by SGE International starting with 3/16" hexagonal stainless steel stock and are 20–30 mm in length, must be large enough to receive miniature nuts and ferrules required for gas-tight compression seals. While the fused silica capillary can heat and cool quickly with simple means such as adjacent heating wires built into the module, the much more massive connectors are not easily heated and temperature cycled through simple means. By incorporating an interface into the module designed for low thermal conductivity over short distances, it is possible to quickly temperature cycle the low thermal mass components of the module outside of the oven while heating the larger thermal mass components within the oven and maintaining an interface in which the oven heat does not significantly conduct external the oven and interfere with the temperature cycling of the module components.

(d) Direct and Conventional Connections of Capillary Column to the Injector and Detector Within the Oven can be Simply Accomplished.

With the oven space open (free of all of the added hardware), there is a large volume to allow a user to easily make separate connections using flexible capillary GC tubing to the injector and detector in the standard manner. These lengths of capillary, approximately 0.3–1 m in length, are then connected to the capillary connectors of the module in the back of the door using standard fittings. Finally, the door is closed for completing the connections to the module. If a module is changed, only the back connections needs to be undone and can be reconnected to a new module.

(e) "Column Cutback" May be Simply Accomplished.

In standard "column cutback" practice, the column is removed from the injector, cut back some length, and then reconnected to the injector. With direct connections inside the oven as in the conventional systems, excess lengths of capillary tubing usually cannot be accommodated requiring the trimming of the column connections to the exact length required to reach the injector and detector. Any need to change the length, whether through accidental breakage of an end or a need to remove a contaminated end of the column may require the entire column and module to be discarded. While in the present invention, the piece of column (free end) connecting the injector to the module is cut back (if it has sufficient length) or simply replaced.

(f) A Single Design can Accommodate all of the Different Possible Injector and Detector Geometries.

One door replacement for a specific model of GC can accommodate all of the possibilities of injector and detector locations within the GC oven. Similarly, a module which operates outside the oven and is inserted through an oven wall allows freedom for the module connections to be made anywhere within the oven.

(g) Multiple GC Modules can be Built into the Design of the Present Invention.

The subject system allows for the inclusion of multiple GC modules due to the simplicity of the interface connections (the existing oven space) and the large size of the existing GC oven being used as an interface. More advanced analyses which split the sample and analyze it simultaneously on two different GC columns and then detect the results with a pair of detectors may easily be accomplished with this design. The subject system simplifies the approaches and increases the possibilities for multicolumn analyses. Not only can multiple temperature programs be run, but the modules may perform unusual temperature programs. The exterior, air-cooled modules can perform multi-segment temperature programs which contain negative ramps as well as positive ramps for advanced applications. The independent temperature programming of multiple modules also allows the sequential operation of columns in series or in combination with valves and individual detectors.

(h) Longer Analytical Column Life for "Column Cutback" Applications.

A difficulty with the standard "column cutback" methods for maintaining the performance of the analytical column with dirty sample methods is that the analytical column becomes progressively shorter with each cutback. Each time the column is cutback, the retention times must be recalibrated since the resistance to carrier gas flow through the column has changed. Eventually, the column becomes too short to provide the required separation performance and must be discarded.

The present invention includes a section of column between the analytical column (contained in the module) and the injector that is easily cutback in the standard manner and replaceable. As a result, the analytical column itself does not need to be cutback if contamination has not reached it. This approach then adds life to the analytical column and cost savings to a user. Further, the GC separation performance may be held more constant since the analytical column is not changing and the length of the connecting column piece can remain unchanged, if needed, by replacement. Many GC column manufacturers actually recommend the use of "guard" column which consists of a length of column before the analytical column which can be changed for this purpose. The design of the system of the present invention incorporates this feature.

(i) The Novel Design can Co-exist with Conventional use of the GC Oven.

If a chromatographer desires to perform an analysis using the GC oven in a conventional manner, a GC module which operates externally to the oven but has connections inserting into the oven will not interfere with the conventional use of the oven. The user simply connects a standard column within the oven between the injector and detector and operates the GC in a standard manner. Further, it is possible to operate both the conventional oven and the external module connected to the oven simultaneously to achieve multidimensional chromatography.

(j) The Design of the Present Invention Permits the Control Electronics for the Alternate GC Column Heating Device to be More Closely Integrated with the GC Column Modules.

The door may also contain the control electronics for the modules, for example. This permits the added instrumentation for the alternate GC column heating to be more compact.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and in certain cases, particular locations of elements may be reversed or interposed, all without departing from the spirit or scope of the invention as defined in the appended claims.

What is claimed is:

1. A gas chromatography (CC) system, comprising:
   (a) a GC oven including an oven cavity enveloped by a walled structure having at least first and a second walls thereof,
      said first wall having at least one module receiving opening defined therein, said second wall having an injector port and a detector port defined therein, and injector and detector connectors extending from said injector and detector ports into said oven cavity;
   (b) at least one GC column module removably secured within said at least one module receiving opening of said first wall and disposed external to said oven cavity, said at least one GC column module including:
      a module housing,
      a capillary column positioned within said module housing and having a main coil and a pair of free ends extending from said main coil,
      a pair of transfer lines, each coupled to a respective one of said free ends of said main coil, said transfer lines for controlling the temperature of said free ends of said main coil in a region adjacent said main coil,
      a heater wire positioned adjacent said transfer lines, and
      means for securing said at least one column module to said first wall;
   (c) first and second GC column lengths positioned within said oven cavity,
      said first and second GC column lengths extending between said module and said injector connector, and said detector connector, respectively; and
   (d) temperature control unit external to said oven cavity and operatively coupled to said heater wire and said transfer lines.

2. The GC system of claim 1, wherein said temperature control unit is attached to said first wall.

3. The GC system of claim 1, wherein said first wall is an oven door, said oven door having hinges located at one side edge thereof for being attached to said walled structure of said oven cavity, and further having a latch mechanism at another side edge of said oven door for hermetically closing said walled structure.

4. The GC system of claim 1, further comprising a pair of chromatography connectors, each coupled to a respective one of said GC capillary free ends from said main coil and extending from said GC column module into said oven cavity, said first and second GC column lengths extending between said chromatography connectors and said injector and detector connectors, respectively.

5. The GC system of claim 1, wherein said first wall further includes an inner plate having feed-through holes defined therein for projection of said free ends of said capillary column therethrough,
   a layer of insulation material attached to said inner plate,
   an insulation retaining plate attached to said layer of insulation material,
   an insulation frame attached to said insulation retaining plate, and
   an outer door attached to said insulation frame,
   each of said layer of insulation material, insulation retaining plate, insulation frame and outer door having at least one slot defined therein in aligned disposition therebetween, said at least one slot defining said at least one module receiving opening of said first wall.

6. The GC system of claim 1, wherein said temperature control unit includes heating control circuits, electrical connections to said at least one module, a microprocessor, and a user interface.

7. The GC system of claim 1, further comprising a plurality of said modules, and wherein said wall has a plurality of said module receiving openings.

8. The GC system of claim 1, further comprising at least one cooling fan attached to said first wall in proximity to said module housing.

9. The GC system of claim 1, wherein said at least one module further comprises:
   a module base plate,
   a module cover attached to said module base plate forming said module housing,
   a module face plate attached to said module housing at one end thereof through a face plate insulation, said module face plate and said face plate insulation having a pair of openings defined therein for projecting said free ends of said capillary column therethrough,
   a pair of module clamps attached to said module face plate in alignment with said openings defined therein, each said module clamp having an aperture provided for a respective one of said free ends of said capillary column to project therethrough.

10. The GC system of claim 9, wherein each of said module clamps includes a clamp spring.

11. The GC system of claim 9, wherein said module housing and said module clamps are formed of perforated stainless steel.

12. The GC system of claim 1, wherein said transfer lines include thin-walled tubes made of steel.

13. The GC system of claim 1, wherein said transfer lines are resistance wire heated tubes sleeving said free ends of said main capillary column.

14. The GC system of claim 1, wherein said heater wire is wound around each of said transfer lines, said transfer lines being heat compensated by reducing the number of heater wire winds around said transfer lines along the length of said transfer lines entering into said oven cavity.

15. The GC system of claim 1, wherein said GC column module comprises:
   a column module, said column module having said module housing containing said main coil therein, said free ends of said capillary column extending beyond said module housing at one end thereof; and a transfer line module, said transfer line module comprising:

a transfer line housing, a pair of said transfer lines secured to and extending through said transfer line housing, said transfer lines sleeving said free ends of said capillary column, a pair of bars extending from said transfer line housing at a face end thereof in proximity to said pair of transfer lines, said chromatography connectors being secured to said rails by means of a bracket sliding therealong; and means for securing said transfer line module to said column module.

16. The GC system of claim 14, wherein said column module and said transfer line module are formed of a perforated stainless steel.

* * * * *